United States Patent
Hwang et al.

(10) Patent No.: US 8,976,919 B2
(45) Date of Patent: Mar. 10, 2015

(54) LOW POWER COMMUNICATION DEVICE FOR SCHEDULING DATA SEGMENTS USING HOLD TIME OR LOCK TIME OF PHASE LOCKED LOOP

(71) Applicant: Samsung Electronics Co., Ltd., Suwon-si (KR)

(72) Inventors: Hyo Sun Hwang, Seoul (KR); Chi Sung Bae, Yongin-si (KR); Young Jun Hong, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 118 days.

(21) Appl. No.: 13/906,615

(22) Filed: May 31, 2013

(65) Prior Publication Data

US 2014/0029652 A1     Jan. 30, 2014

(30) Foreign Application Priority Data

Jul. 27, 2012   (KR) .................. 10-2012-0082075

(51) Int. Cl.
| | | |
|---|---|---|
| H04L 7/00 | (2006.01) | |
| H03D 3/24 | (2006.01) | |
| H04L 7/033 | (2006.01) | |
| H03L 7/00 | (2006.01) | |
| A61B 5/00 | (2006.01) | |
| H04L 1/18 | (2006.01) | |
| A61B 5/024 | (2006.01) | |
| A61B 5/08 | (2006.01) | |

(52) U.S. Cl.
CPC ............. *H04L 7/0331* (2013.01); *H04L 7/033* (2013.01); *H03L 7/00* (2013.01); *A61B 5/0022* (2013.01); *H04L 1/1864* (2013.01); *H04L 7/0083* (2013.01); *A61B 5/002* (2013.01); *A61B 5/0024* (2013.01); *A61B 5/024* (2013.01); *A61B 5/0816* (2013.01)
USPC .......................................... 375/354; 375/376

(58) Field of Classification Search
USPC ................ 375/316, 259, 354, 371, 373, 376; 708/208, 209; 370/252
See application file for complete search history.

(56) References Cited

U.S. PATENT DOCUMENTS

| | | | |
|---|---|---|---|
| 4,536,876 A | 8/1985 | Bahr et al. | |
| 6,456,887 B1 * | 9/2002 | Dudding et al. | ........... 607/60 |
| 7,620,138 B2 * | 11/2009 | Muta | .............. 375/372 |

FOREIGN PATENT DOCUMENTS

| | | |
|---|---|---|
| KR | 2000-0003083 | 1/2000 |
| KR | 2003-0038208 | 5/2003 |
| KR | 2003-0075195 | 9/2003 |
| KR | 10-2005-0004288 | 1/2005 |
| KR | 10-2005-0027131 | 3/2005 |
| KR | 10-2010-0068059 | 6/2010 |

* cited by examiner

*Primary Examiner* — Vineeta Panwalkar
(74) *Attorney, Agent, or Firm* — NSIP Law (57) ABSTRACT

A device communicating with a node, includes a communication unit configured to transmit a transmitting data segment to the node, and receive a receiving data segment from the node. The device further includes a phase locked loop (PLL) configured to generate an operating frequency for the communication unit. The device further includes a PLL controller configured to control a hold time and a lock time, of the PLL, that are shared between the node and the device. The device further includes a scheduler configured to schedule the transmitting data segment and the receiving data segment based on the controlled hold time and lock time.

20 Claims, 8 Drawing Sheets

LOW POWER COMMUNICATION DEVICE FOR SCHEDULING DATA SEGMENTS USING HOLD TIME OR LOCK TIME OF PHASE LOCKED LOOP

CROSS-REFERENCE TO RELATED APPLICATION

This application claims the benefit under 35 USC 119(a) of Korean Patent Application No. 10-2012-0082075, filed on Jul. 27, 2012, in the Korean Intellectual Property Office, the entire disclosure of which is incorporated herein by reference for all purposes.

BACKGROUND

1. Field

The following description relates to a low power communication device for scheduling data segments using a hold time or a lock time of a phase locked loop (PLL).

2. Description of Related Art

Studies have been conducted on a wireless network used to sense a biometric signal from a patient or a user, and to collect the sensed biometric signal. The wireless network may include a sensing unit that senses the biometric signal from the patient or the user, and a master node that receives data segments from the sensing unit and transmits a control signal to the sensing unit. The wireless network may further include a server that manages biometric signals collected from sensing units, and an expert terminal that accesses the server to perform an expert analysis of a biometric signal of a desired patient or user. The master node may correspond to a mobile terminal. In such a network, use of the sensing unit or the master node may be needed for low power consumption.

SUMMARY

In one general aspect, there is provided a device communicating with a node, the device including a communication unit configured to transmit a transmitting data segment to the node, and receive a receiving data segment from the node. The device further includes a phase locked loop (PLL) configured to generate an operating frequency for the communication unit. The device further includes a PLL controller configured to control a hold time and a lock time, of the PLL, that are shared between the node and the device. The device further includes a scheduler configured to schedule the transmitting data segment and the receiving data segment based on the controlled hold time and lock time.

In another general aspect, there is provided a device communicating with a node, the device including a sensor unit configured to sense a biometric signal. The device further includes a communication unit configured to transmit, to the node, a transmitting data segment of the biometric signal, and receive, from the node, a receiving data segment. The device further includes a phase locked loop (PLL) configured to generate an operating frequency for the communication unit. The device further includes a PLL controller configured to control a hold time and a lock time, of the PLL, that are shared between the node and the device. The device further includes a scheduler configured to schedule the transmitting data segment and the receiving data segment based on the controlled hold time and lock time.

In still another general aspect, there is provided a device communicating with a node, the device including a communication unit configured to transmit a transmitting data segment to the node. The device further includes a phase locked loop (PLL) configured to generate an operating frequency for the communication unit. The device further includes a PLL controller configured to control a hold time and a lock time, of the PLL, that are shared between the node and the device. The device further includes a scheduler configured to schedule the transmitting data segment based on the controlled hold time and lock time.

Other features and aspects will be apparent from the following detailed description, the drawings, and the claims.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 1:
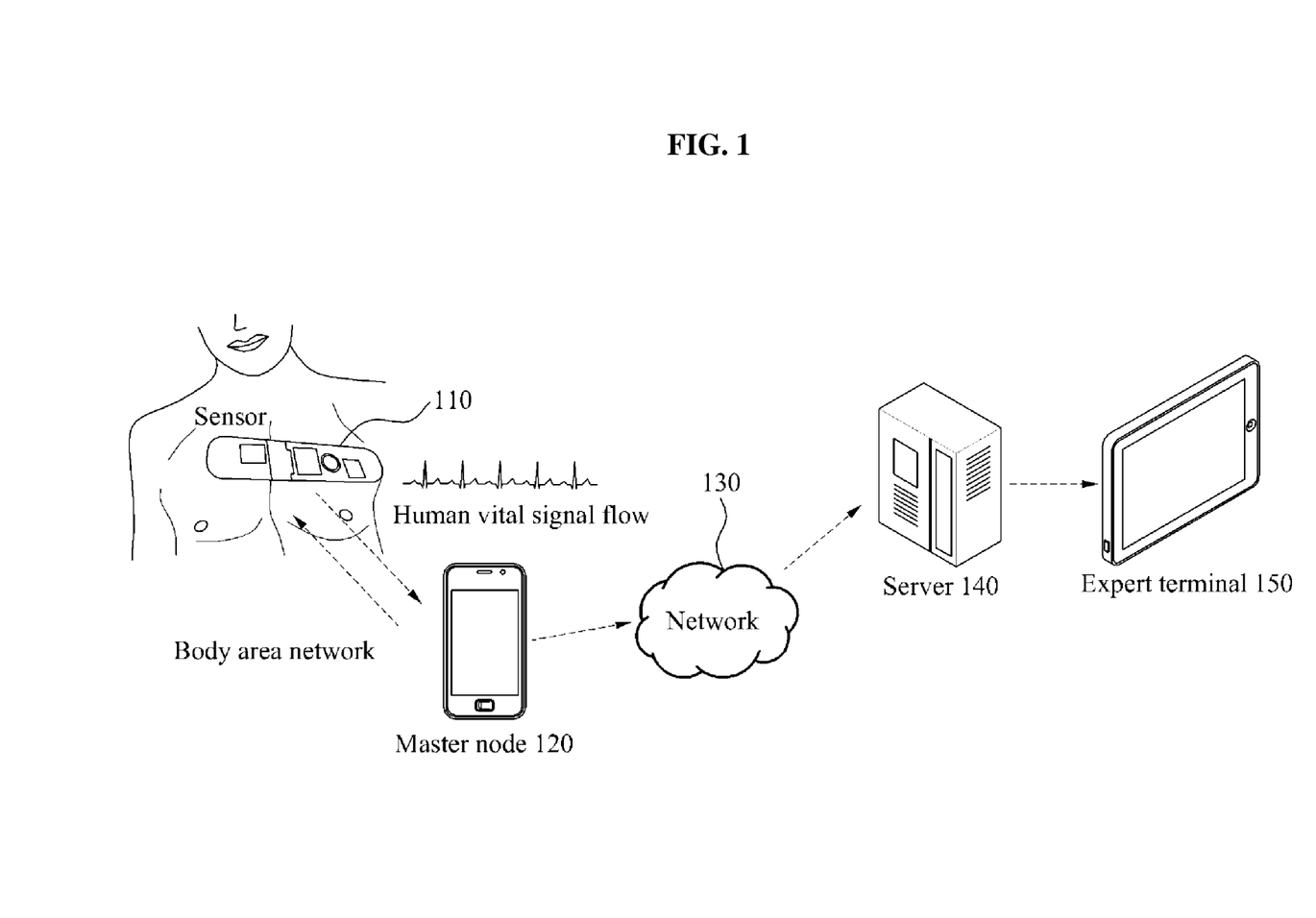
FIG. 1 is a diagram illustrating an example of a wireless communication network that collects a biometric signal.

FIG. 1 is a diagram illustrating an example of a wireless communication network that collects a biometric signal. Referring to FIG. 1, the wireless communication network includes a sensor unit 110, a master node 120, a network 130, a server 140, and an expert terminal 150.

The sensor unit 110 senses a biometric signal from a user, for example, a patient, and transmits the sensed biometric signal to the master node 120. For example, the sensor unit 110 may be in a body area network within, on, and/or in a proximity of the user. The biometric signal may include a human vital signal flow, such as, for example, a pulse rate, a heart rate, a respiratory rate, a body temperature, and/or a blood pressure.

The master node 120 may include, for example, an access point, a gateway, a femto base station, a relay station, a mobile device (e.g., a smartphone), and/or other devices known to one of ordinary skill in the art. The master node 120 transmits the biometric signal to the server 140 via the network 130, and the expert terminal 150 accesses the server 140 to obtain biometric signals from users.

The sensor unit 110 may need low power consumption. However, the sensor unit 110 may include, for example, radio frequency (RF) processing units that consume a considerable amount of power. In this example, each of the RF processing units may include a wireless communication unit. The wireless communication unit may need to operate at a predetermined (e.g., fixed) operating frequency, and a phase locked loop (PLL) may provide the predetermined operating frequency to the wireless communication unit. Since the wireless communication unit may need to operate at the predetermined operating frequency in a high frequency band, it may be difficult to reduce power consumption of the PLL. Accordingly, reducing the power consumption of the PLL may be an issue.

Figure 2:
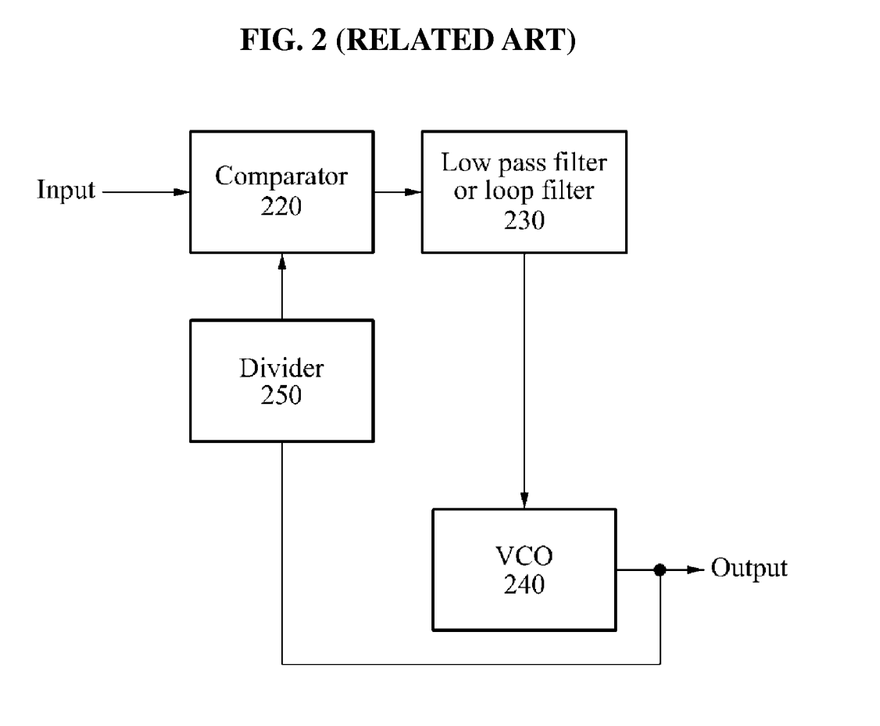
FIG. 2 is a block diagram illustrating a phase locked loop (PLL) according to a related art.

FIG. 2 is a block diagram illustrating an example of a PLL according to a related art. Referring to FIG. 2, the PLL includes a comparator 220, a low pass filter or a loop filter 230, a voltage controlled oscillator (VCO) 240, and a divider 250. The comparator 220 compares an output frequency divided by the divider 250 to an input frequency, and the filter 230 and the VCO 240 control the output frequency based on a result of the comparison. Accordingly, the output frequency may be maintained uniformly.

Figure 3:
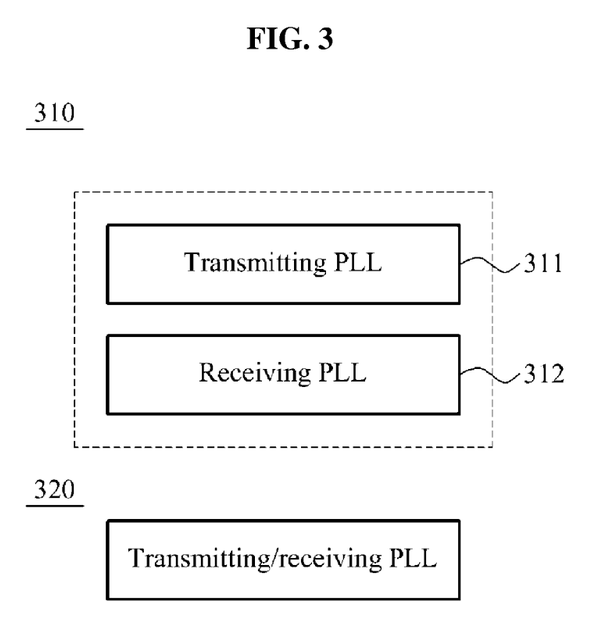
FIG. 3 is a block diagram illustrating examples of PLLs.

FIG. 3 is a block diagram illustrating examples of PLLs 310 and 320. Referring to FIG. 3, each of the PLLs 310 and 320 provides a predetermined operating frequency to each of a transmitting wireless communication unit and a receiving wireless communication unit, of a low power communication device, for example, a sensing device. The PLL 310 includes a transmitting PLL 311 and a receiving PLL 312 that provide predetermined operating frequencies to the transmitting wireless communication unit and the receiving wireless communication unit, respectively. The PLL 320 includes a combination of the transmitting PLL 311 and the receiving PLL 312.

Figure 4:
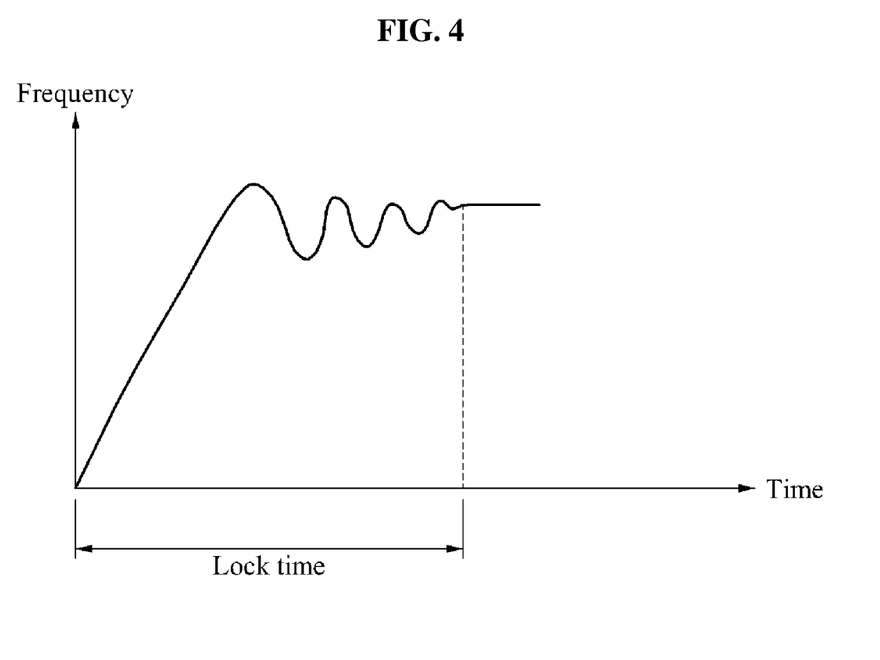
FIG. 4 is a graph illustrating an example of a PLL lock time.

FIG. 4 is a graph illustrating an example of a PLL lock time. Referring to FIG. 4, a predetermined period of time is needed for a PLL to generate a predetermined operating frequency that is unchanged and maintained when operation of the PLL is initiated. Such a predetermined period of time is termed the PLL lock time.

During the operation of the PLL, the PLL may continuously output the predetermined operating frequency. When the operation of the PLL is stopped, the PLL outputs an output frequency that is unchanged and maintained for a predetermined period of time, and when the predetermined period of time elapses, the PLL outputs an output frequency that is variably changed. This predetermined period of time during which the output frequency is maintained is termed a PLL hold time.

Figure 5:
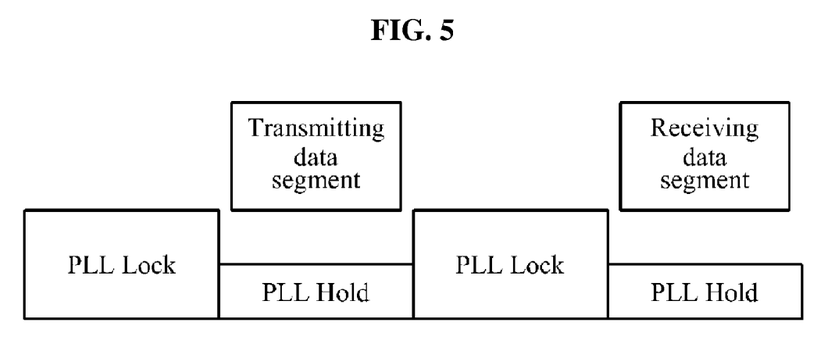
FIG. 5 is a diagram illustrating an example of data segments scheduled during a PLL hold time.

FIG. 5 is a diagram illustrating an example of data segments scheduled during a PLL hold time. Referring to FIG. 5, a sensing device or a low power communication device allocates at least one transmitting data segment to be transmitted by a transmitting wireless communication unit during the PLL hold time of a transmitting PLL that provides a predetermined operating frequency to the transmitting wireless communication unit. That is, the sensing device controls the PLL hold time by properly turning ON/OFF the transmitting PLL, and transmits the transmitting data segment during the controlled PLL hold time, to reduce power consumption of the transmitting PLL.

In more detail, the sensing device turns ON the transmitting PLL, and a PLL lock time of the transmitting PLL starts. When the PLL lock time elapses, the sensing device turns OFF the transmitting PLL, and the PLL hold time starts. During the PLL hold time, the sensing device transmits the transmitting data segment.

In the same manner as the transmitting PLL, the sensing device controls another PLL hold time of a receiving PLL by properly turning ON/OFF the receiving PLL. The receiving PLL provides a predetermined operating frequency to a receiving wireless communication unit of the sensing device. The sensing device further receives at least one receiving data segment via the receiving wireless communication unit during the other PLL hold time, to reduce power consumption of the receiving PLL.

In more detail, when the PLL hold time of the transmitting PLL elapses, the sensing device turns ON the receiving PLL, and another PLL lock time of the receiving PLL starts. When the other PLL lock time elapses, the sensing device turns OFF the receiving PLL, and the other PLL hold time starts. During the other PLL hold time, the sensing device receives the receiving data segment.

Figure 6:
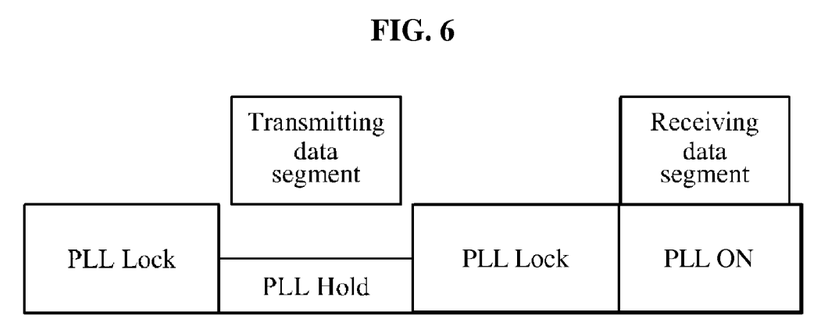
FIG. 6 is a diagram illustrating an example of a data segment scheduled during a PLL hold time.

FIG. 6 is a diagram illustrating an example of a data segment scheduled during a PLL hold time. Referring to FIG. 6, a sensing device or a low power communication device allocates at least one transmitting data segment to be transmitted by a transmitting wireless communication unit during the PLL hold time of a transmitting PLL that provides a predetermined operating frequency to the transmitting wireless communication unit, as described with reference to FIG. 5.

When the PLL hold time elapses, the sensing device turns ON a receiving PLL that provides a predetermined operating frequency to a receiving wireless communication unit, and a PLL lock time of the receiving PLL starts. When the sensing device keeps ON the receiving PLL, the receiving PLL fails to be placed in a hold condition, e.g., another PLL hold time of the receiving PLL fails to start. Nonetheless, when the PLL lock time elapses, the sensing device receives at least one receiving data segment via the receiving wireless communication unit, even though the receiving PLL is kept ON.

Figure 7:
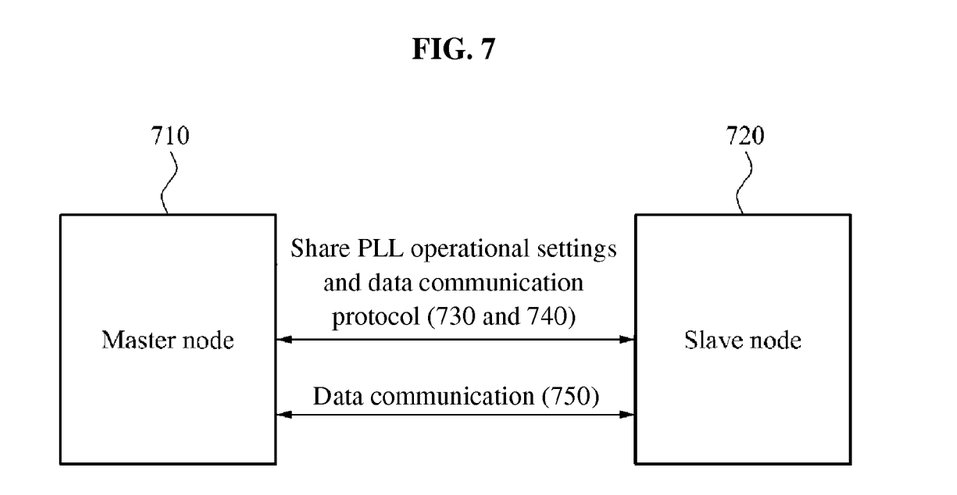
FIG. 7 is a block diagram illustrating an example of a master node and a salve node.

FIG. 7 is a block diagram illustrating an example of a master node 710 and a slave node 720. Referring to FIG. 7, the master node 710 and the slave node 720, of a network, perform data communication after sharing PLL operational settings and information on a data communication protocol. The slave node 720 may correspond to a low power communication device, such as, for example, a sensing device. Operations of the slave node 720 that are described herein may also be performed by the master node 710, and vice versa.

To apply the examples described herein to communication nodes or nodes within a network, information sharing between the nodes is needed in advance. Among two communication nodes or nodes within a network, a node taking the lead in time synchronization within the network may be referred to as a master node, and a node operating in compliance with the time synchronization achieved by the master node may be referred to as a slave node. Referring again to FIG. 7, a procedure of information sharing between the master node 710 and the slave node 720 is performed as described herein.

In operation 730, the slave node 720 determines and transmits, to the master node 710, PLL operational settings of the slave node 720, and information on a data communication protocol, for example, an automatic repeat request (ARQ) protocol, of the slave node 720. For example, the PLL operational settings may include a PLL lock time of at least one PLL (TPLL_LOCK), and a PLL hold time of the PLL (TPLL_HOLD). The information on the data communication protocol may include, for example, information on the ARQ protocol, including an I-ACK (mandatory) acknowledgement policy, an n-ACK (option) acknowledgement policy, or an B-ACK (option) acknowledgement policy. The I-ACK acknowledgement policy instructs or commands the slave node 720 to receive an ACK (acknowledgement) message immediately after transmitting a data segment or frame. The n-ACK acknowledgement policy instructs or commands the slave node 720 to receive an ACK message after transmitting n data segments or frames where n may include a predetermined value within an allowable range. The B-ACK acknowledgement policy instructs or commands the slave node 720 to receive an ACK message after transmitting a predetermined block of data segments or frames.

In operation 740, the master node 710 determines and transmits, to the slave node 720, PLL operational settings and information on a data communication protocol, for example, the ARQ protocol, to be used by the entire network and/or by a predetermined slave node, e.g., the slave node 720. Among values corresponding to all slave nodes, the master node 710 may select a maximum value to be a PLL lock time of at least one PLL for a slave node, and a minimum value to be a PLL hold time of the PLL.

In operation 750, the master node 710 and the slave node 720 perform the data transmission based on the PLL operational settings and the information on the data communication protocol, which is shared between the master node 710 and the slave node 720. The master node 710 and the slave node 720 may apply the PLL operational settings to a data segment or frame or a predetermined group of data segments or frames, based on a medium access control (MAC) protocol for wireless communication or a mobile application part (MAP) protocol, as predetermined and described herein.

Figure 8:
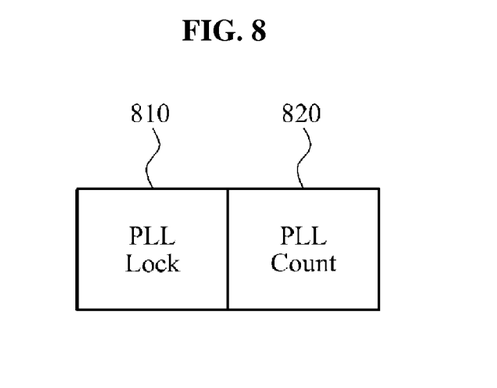
FIG. 8 is a diagram illustrating an example of a frame header, including a PLL lock indicator and a PLL count indicator, in a data segment.

FIG. 8 is a diagram illustrating an example of a frame header, including a PLL lock indicator 810 and a PLL count indicator 820, in a data segment. Referring to FIG. 8, to apply PLL operational settings to the data segment or frame, the frame header (e.g., a frame control field) may be used or set by, e.g., a master node or a slave node. The frame header may be used as a PLL control field in an interchangeable manner.

In more detail, the PLL lock indicator 810 indicates whether a PLL of a node that receives the corresponding frame is to be turned ON. For example, when the PLL lock indicator 810 is set to a value corresponding to ON, the PLL may be turned ON when the corresponding frame is completely processed (e.g., received) or when a predetermined period of time elapses. In this example, the PLL count indicator 820 may be set to a value of 0.

The PLL count indicator 820 indicates a number of frames to be processed (e.g., received), subsequent to processing (e.g., reception) of the corresponding frame, before turning ON the PLL. For example, when the PLL count indicator 820 is set to a value of 2, the PLL may be turned ON when two frames are completely processed (e.g., received), subsequent to processing (e.g., reception) of the corresponding frame. When the PLL count indicator 820 is set to a value of 1 or more, the PLL lock indicator 810 may be set to a value corresponding to OFF. When the PLL count indicator 820 is set to a value of 0, the PLL lock indicator 810 may be set to value corresponding to ON.

Figure 9:
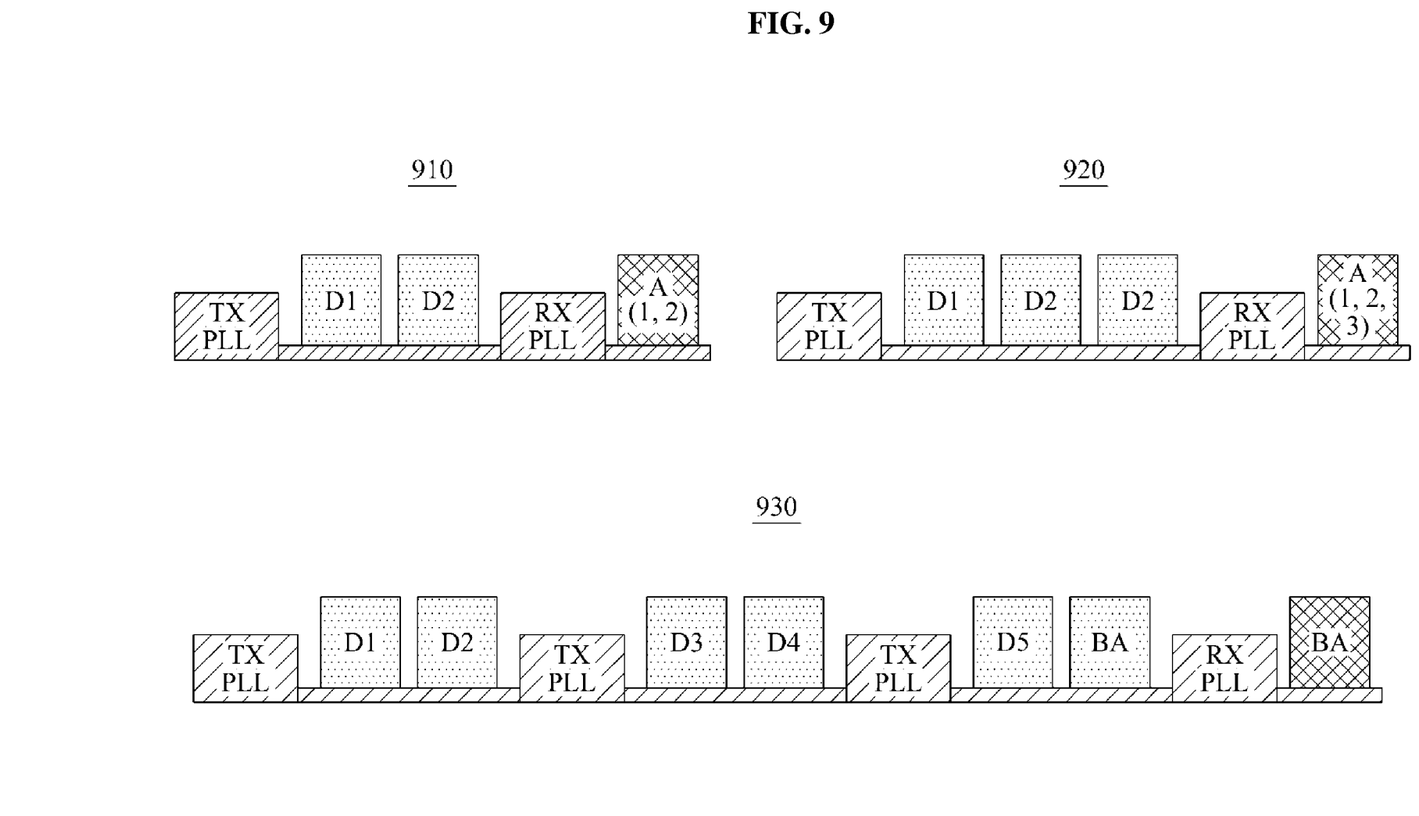
FIG. 9 is a diagram illustrating an example of a method of controlling a PLL hold time or a PLL lock time with an automatic repeat request (ARQ) protocol.

FIG. 9 is a diagram illustrating an example of a method of controlling a PLL hold time or a PLL lock time with an ARQ protocol. When a lower power communication device is to turns ON a PLL, the low power communication device determines whether a transmitting PLL or a receiving PLL is to be turned ON based on the ARQ protocol applied to a corresponding frame to be transmitted or received. For example, referring to FIG. 9, in a graph 910, a receiving PLL (RX PLL) is turned ON to receive an ACK message A (1, 2) after a second data frame D2 is transmitted, based on an n-ACK acknowledgement policy. In a graph 920, a receiving PLL is turned ON to receive an ACK message (A, 1, 2, 3) after a third data frame D2 is transmitted, based on an n-ACK acknowledgment policy. In a graph 930, a transmitting PLL (TX PLL) is turned ON to transmit a fifth data frame D5 after a second data frame D2 and a fourth data frame D4 are transmitted, based on an B-ACK acknowledgement policy. A receiving PLL is turned on to receive an ACK message (BA) after the fifth data frame D5 is transmitted, based on the B-ACK acknowledgement policy. In other words, the ARQ protocol is considered when controlling an operation of a PLL.

In a wireless communication system, a link adaptation method may determine a frame length and a frame rate based on a channel state. The PLL hold time of at least one PLL may be set in an initialization of the system. However, a number of frames to be transmitted during the PLL hold time may be determined based on the channel state. Accordingly, a master node may control a data communication protocol, for example, the ARQ protocol, and PLL operational settings, to be used by a slave node.

The master node may adaptively determine the ARQ protocol based on the channel state. The master node may recognize the channel state based on either a MAC retransmission rate or a channel state received from a physical (PHY) layer, for example, a channel state information (CSI) value and/or a received signal strength indication (RSSI) value. When the channel state is poor, the master node may decrease a frame transmission rate and/or a payload size. When the channel state is good, the master node may increase the frame transmission rate and/or the payload size. When the frame transmission rate is reduced or the payload size is increased, a frame transmission time may be increased, and a number of frames to be transmitted during the PLL hold time may be decreased. In the n-ACK acknowledgement policy, the master node may increase an n value, and in the B-ACK acknowledgement policy, the master node may increase a number of frames to be transmitted concurrently. A communication node may set a PLL control field based on the determined ARQ protocol, including, e.g., the number of frames to be transmitted concurrently.

Figure 10:
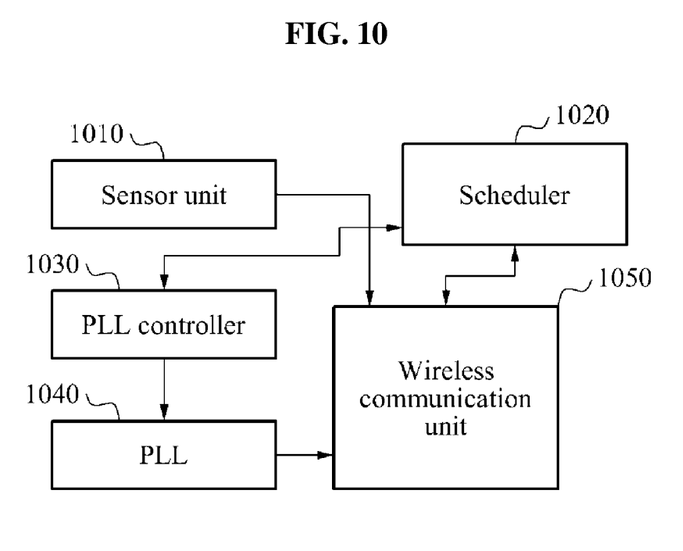
FIG. 10 is a block diagram illustrating an example of a low power communication device.

FIG. 10 is a block diagram illustrating an example of a low power communication device. Referring to FIG. 10, the low power communication device communicates with a master node, and includes a sensor unit 1010, a scheduler 1020, a PLL controller 1030, a PLL 1040, and a wireless communication unit 1050.

The sensor unit 1010 senses a biometric signal from a user or patient. For example, the biometric signal may include a pulse rate, a heart rate, a respiratory rate, a body temperature, and/or a blood pressure.

The wireless communication unit 1050 transmits, to the master node, at least one transmitting data segment of the biometric signal, and receives, from the master node, at least one receiving data segment. The wireless communication unit 1050 may include a transmitting wireless communication unit that transmits the at least one transmitting data segment, and/or a receiving wireless communication that receives the at least one receiving data segment.

The wireless communication unit 1050 shares (e.g., transmits and receives), with the master node in advance, PLL operational settings of the PLL 1040, and information on a data communication protocol (e.g., an ARQ protocol) of the low power communication device. For example, the PLL operation settings may include an original hold time and an original lock time, of the PLL 1040, and may be determined based on operation characteristics of the PLL 1040 and/or an PLL included in another low power communication device. The information on the data communication protocol may include, for example, a number of transmitting data segments to be transmitted continuously by the low power communication device before receiving a receiving data segment, e.g., an ACK message.

The PLL 1040 generates and provides a predetermined operating frequency to the wireless communication unit 1050. For example, the PLL 1040 may include a receiving PLL and/or a transmitting PLL that generate and provide predetermined operating frequencies to the receiving wireless communication unit and the transmitting wireless communication unit, respectively.

The PLL controller 1030 controls a PLL hold time and a PLL lock time, of the PLL 1040, based on the PLL operational settings being shared in advance between the master node and the low power communication device.

The scheduler 1020 schedules the at least one transmitting data segment and the at least one receiving data segment based on the controlled PLL hold time and/or PLL lock time, and/or the data communication protocol shared in advance between the master node and the low power communication device. For example, the scheduler 1020 may adjust a number of transmitting data segments and receiving data segments to be adaptively scheduled within the controlled PLL hold time based on a channel state, an amount of interference, and/or an amount of traffic, between the low power communication device and the master node.

The wireless communication unit 1050 may transmit, to the master node, a PLL lock indicator indicating whether at least one PLL of the master node is to be locked or turned ON when the node completely processes (e.g., receives) a corresponding data segment, including the PLL lock indicator, or when a predetermined period of time elapses from a time that the node completely processes the corresponding data segment. The wireless communication unit 1050 may further transmit, to the master node, a PLL count indicator indicating a number of data segments to be processed (e.g., received) by the node, subsequent to the node processing the corresponding data segment including the PLL count indicator, before the at least one PLL of the master node is to be locked. The PLL lock indicator and the PLL count indicator may be transmitted, to the master node, via a frame header of the at least one transmitting data segment transmitted to the master node.

The wireless communication unit 1050 may receive, from the master node, a PLL lock indicator indicating whether at least one PLL of the low power communication device is to be locked or turned ON when the low power communication device completely processes (e.g., receives) a corresponding data segment, including the PLL lock indicator, or when a predetermined period of time elapses from a time that the low power communication device completely processes the corresponding data segment. The wireless communication unit 1050 may further receive, from the master node, a PLL count indicator indicating a number of data segments to be processed by the low power communication device, subsequent to the low power communication device processing the corresponding data segment including the PLL count indicator, before the at least one PLL of the low power communication device is to be locked. The PLL lock indicator and the PLL count indicator may be received, from the master node, via a frame header of the at least one received data segment received from the master node.

The various units and methods described above may be implemented using one or more hardware components, one or more software components, or a combination of one or more hardware components and one or more software components.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may include various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions that control a processing device to implement a software component may include a computer program, a piece of code, an instruction, or some combination thereof, that independently or collectively instructs or configures the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments that implement the examples disclosed herein can be easily constructed by a programmer skilled in the art to which the examples pertain based on the drawings and their corresponding descriptions as provided herein.

As a non-exhaustive illustration only, a terminal and device described herein may be a mobile device, such as a cellular phone, a personal digital assistant (PDA), a digital camera, a portable game console, an MP3 player, a portable/personal multimedia player (PMP), a handheld e-book, a portable laptop PC, a global positioning system (GPS) navigation device, a tablet, a sensor, or a stationary device, such as a desktop PC, a high-definition television (HDTV), a DVD player, a Blue-ray player, a set-top box, a home appliance, or any other device known to one of ordinary skill in the art that is capable of wireless communication and/or network communication.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A device communicating with a node, the device comprising:
   a communication unit configured to transmit a transmitting data segment to the node, and receive a receiving data segment from the node;
   a phase locked loop (PLL) configured to generate an operating frequency for the communication unit;
   a PLL controller configured to control a hold time and a lock time, of the PLL, that are shared between the node and the device; and
   a scheduler configured to schedule the transmitting data segment and the receiving data segment based on the controlled hold time and lock time.

2. The device of claim 1, wherein the hold time and the lock time are determined based on an operating characteristic of the PLL and/or an operating characteristic of a PLL of another device.

3. The device of claim 1, wherein the scheduler is further configured to:
   schedule the transmitting data segment and the receiving data segment further based on information on a data communication protocol that is shared between the node and the device.

4. The device of claim 3, wherein the information on the data communication protocol comprises a number of transmitting data segments to be transmitted continuously before receiving an acknowledgement message.

5. The device of claim 3, wherein the data communication protocol comprises an automatic repeat request (ARQ) protocol.

6. The device of claim 1, wherein the PLL comprises:
   a first PLL configured to generate an operating frequency for the communication unit to receive the receiving data segment, and/or a second PLL configured to generate an operating frequency for the communication unit to transmit the transmitting data segment.

7. The device of claim 1, wherein the scheduler is further configured to:
   adjust a number of transmitting data segments and receiving data segments to be scheduled within the controlled hold time.

8. The device of claim 7, wherein the scheduler is further configured to:
   adjust the number of transmitting data segments and receiving data segments to be scheduled within the controlled hold time based on a channel state, or an amount of interference, or an amount of traffic, or any combination thereof, between the device and the node.

9. The device of claim 1, wherein the communication unit is further configured to:
   transmit, to the node, a PLL lock indicator indicating whether a PLL of the node is to be locked in response the node processing a corresponding data segment, or in response to a predetermined period of time elapsing from a time that the node processes the corresponding data segment.

10. The device of claim 1, wherein the communication unit is further configured to:
transmit, to the node, a PLL count indicator indicating a number of data segments to be processed by the node, subsequent to the node processing a corresponding data segment, before a PLL of the node is to be locked.

11. The device of claim 1, wherein the communication unit is further configured to:
receive, from the node, a PLL lock indicator indicating whether the PLL is to be locked in response to the device processing a corresponding data segment, or in response to a predetermined period of time elapsing from a time that the device processes the corresponding data segment.

12. The device of claim 1, wherein the communication unit is further configured to:
receive, from the node, a PLL count indicator indicating a number of data segments to be processed by the device, subsequent to the device processing a corresponding data segment, before the PLL is to be locked.

13. The device of claim 1, wherein the hold time comprises a predetermined period of time during which the operating frequency is maintained in response to operation of the PLL being stopped.

14. The device of claim 1, wherein the lock time comprises a predetermined period of time for the PLL to generate and maintain the operating frequency in response to operation of the PLL being initiated.

15. The device of claim 1, wherein the scheduler is further configured to:
schedule the transmitting data segment to be transmitted during the controlled hold time.

16. The device of claim 1, wherein the scheduler is further configured to:
schedule the receiving data segment to be received during the controlled hold time and/or in response to the controlled lock time elapsing and the PLL being on.

17. A device communicating with a node, the device comprising:
a sensor unit configured to sense a biometric signal;
a communication unit configured to transmit, to the node, a transmitting data segment of the biometric signal, and receive, from the node, a receiving data segment;
a phase locked loop (PLL) configured to generate an operating frequency for the communication unit;
a PLL controller configured to control a hold time and a lock time, of the PLL, that are shared between the node and the device; and
a scheduler configured to schedule the transmitting data segment and the receiving data segment based on the controlled hold time and lock time.

18. A device communicating with a node, the device comprising:
a communication unit configured to transmit a transmitting data segment to the node;
a phase locked loop (PLL) configured to generate an operating frequency for the communication unit;
a PLL controller configured to control a hold time and a lock time, of the PLL, that are shared between the node and the device; and
a scheduler configured to schedule the transmitting data segment based on the controlled hold time and lock time.

19. The device of claim 18, wherein the scheduler is further configured to:
schedule the transmitting data segment further based on information on an automatic repeat request (ARQ) protocol that is shared between the node and the device.

20. The device of claim 18, wherein the scheduler is further configured to:
adjust a number of transmitting data segments to be scheduled within the controlled hold time based on a channel state, or an amount of interference, or an amount of traffic, or any combination thereof, between the device and the node.

* * * * *